US00PP29224P2

(12) United States Plant Patent
Nebelmeir

(10) Patent No.: US PP29,224 P2
(45) Date of Patent: Apr. 10, 2018

(54) POINSETTIA PLANT NAMED 'LAZZPO1315'

(50) Latin Name: ***Euphorbia pulcherrima* Willd.**
Varietal Denomination: LAZZPO1315

(71) Applicant: Johannes Nebelmeir, Marling (IT)

(72) Inventor: Johannes Nebelmeir, Marling (IT)

(73) Assignee: Lazzeri Societa Agricola a.r.l., Sabaudia (IT)

( * ) Notice: Subject to any disclaimer, the term of this patent is extended or adjusted under 35 U.S.C. 154(b) by 0 days.

(21) Appl. No.: 15/530,658

(22) Filed: Feb. 16, 2017

(51) Int. Cl.
*A01H 5/02* (2006.01)

(52) U.S. Cl.
USPC ..... Plt./304

(58) Field of Classification Search
USPC ..... Plt./304, 305
CPC ..... A01H 5/0244
See application file for complete search history.

*Primary Examiner* — Kent L Bell
(74) *Attorney, Agent, or Firm* — C. A. Whealy

(57) ABSTRACT

A new and distinct cultivar of Poinsettia plant named 'LAZZPO1315', characterized by its compact to medium-size, broadly upright and uniformly mounding plant habit; moderately vigorous growth habit; freely branching habit; dark green-colored leaves; large and full inflorescences with very light yellow-colored flower bracts that appear almost white in color; and excellent post-production longevity.

2 Drawing Sheets

Botanical designation: *Euphorbia pulcherrima* Willd.
Cultivar denomination: 'LAZZPO1315'.

BACKGROUND OF THE INVENTION

The present invention relates to a new and distinct cultivar of Poinsettia plant, botanically known as *Euphorbia pulcherrima* Willd. and hereinafter referred to by the name 'LAZZPO1315'.

The new Poinsettia plant is a product of a planned breeding program conducted by the Inventor in Merano, Italy. The objective of the breeding program is to create new compact and freely-branching Poinsettia plants with white-colored flower bracts.

The new Poinsettia plant originated from a polycross made by the Inventor in 2010 in Merano, Italy of a proprietary selection of *Euphorbia pulcherrima* Willd. identified as code number 2008/255-004, not patented, as the female, or seed, parent with mixed pollen from a number of *Euphorbia pulcherrima* Willd. proprietary selections and commercial varieties with white-colored flower bracts as the male, or pollen, parent. The new Poinsettia plant was discovered and selected by the Inventor as a single flowering plant within the progeny of the stated polycross in a controlled greenhouse environment in Merano, Italy in December, 2011.

Asexual reproduction of the new Poinsettia plant by terminal vegetative cuttings in a controlled greenhouse environment in Merano, Italy since May, 2012 has shown that the unique features of this new Poinsettia plant are stable and reproduced true to type in successive generations of asexual reproduction.

SUMMARY OF THE INVENTION

Plants of the new Poinsettia have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'LAZZPO1315'. These characteristics in combination distinguish 'LAZZPO1315' as a new and distinct Poinsettia plant:

1. Compact to medium-size, broadly upright and uniformly mounding plant habit.
2. Moderately vigorous growth habit.
3. Freely branching habit.
4. Dark green-colored leaves.
5. Large and full inflorescences with very light yellow-colored flower bracts that appear almost white in color.
6. Excellent post-production longevity.

Plants of the new Poinsettia can be compared to plants of the female parent selection. Plants of the new Poinsettia differ primarily from plants of the female parent selection in plant performance as plants of the female parent selection are not suitable for typical commercial greenhouse Poinsettia production.

Plants of the new Poinsettia can be compared to plants of *Euphorbia pulcherrima* Willd. 'Duegla13', disclosed in U.S. Plant Pat. No. 26,094. In side-by-side comparisons, plants of the new Poinsettia differ primarily from plants of 'Duegla13' in the following characteristics:

1. Plants of the new Poinsettia are more compact than plants of 'Duegla13'.
2. Leaves of plants of the new Poinsettia are darker green in color than leaves of plants of 'Duegla13'.
3. Flower bracts of plants of the new Poinsettia are "whiter" in color than flower bracts of 'Duegla13'.

Plants of the new Poinsettia can be compared to plants of *Euphorbia pulcherrima* Willd. 'OGLPNT14001', disclosed in U.S. Plant Pat. No. 21,715. In side-by-side comparisons, plants of the new Poinsettia differ primarily from plants of 'OGLPNT14001' in the following characteristics:

1. Plants of the new Poinsettia are more compact than plants of 'OGLPNT14001'.
2. Leaves of plants of the new Poinsettia are darker green in color than leaves of plants of 'OGLPNT14001'.
3. Flowers bracts of plants of the new Poinsettia are slightly smaller than flower bracts of plants of 'OGLPNT14001'.
4. Flower bracts of plants of the new Poinsettia are "whiter" in color than flower bracts of 'OGLPNT14001'.

BRIEF DESCRIPTION OF THE PHOTOGRAPHS

The accompanying photographs illustrate the overall appearance of the new Poinsettia plant showing the colors as true as it is reasonably possible to obtain in colored reproductions of this type. Colors in the photographs may differ slightly from the color values cited in the detailed botanical description which accurately describe the colors of the new Poinsettia plant.

The photograph on the first sheet comprises a side perspective view of a typical flowering plant of 'LAZZPO1315' grown in a container.

The photographs on the second sheet are close-up views of a typical inflorescence and the upper and lower surfaces of transitional and fully expanded flower bracts of 'LAZZPO1315'.

DETAILED BOTANICAL DESCRIPTION

The aforementioned photographs and following observations and measurements describe plants grown during the summer to winter in 15-cm containers in a glass-covered greenhouse in Merano, Italy and under cultural practices typical of commercial Poinsettia production. During the production of the plants, day temperatures ranged from 15° C. to 20° C., night temperatures ranged from 10° C. to 15° C. and light levels ranged from 40 to 55 klux. Plants were pinched one time two weeks after planting and were five months old when the photographs and the detailed description were taken. In the following description, color references are made to The Royal Horticultural Society Colour Chart, 1995 Edition, except where general terms of ordinary dictionary significance are used.

Botanical classification: *Euphorbia pulcherrima* Willd. 'LAZZPO1315'.

Parentage:

*Female, or seed, parent*.—Proprietary selection of *Euphorbia pulcherrima* Willd. identified as code number 2008/255-004, not patented.

*Male, or pollen, parent*.—Mixed pollen from a number of *Euphorbia pulcherrima* Willd. proprietary selections and commercial varieties with white-colored flower bracts.

Propagation:

*Type*.—Terminal vegetative cuttings.

*Time to initiate roots, summer*.—About two weeks at soil temperatures ranging from 22° C. to 25° C. and ambient temperatures ranging from 25° C. to 30° C.

*Time to produce a rooted young plant, summer*.—About four weeks at soil temperatures ranging from 22° C. to 25° C. and ambient temperatures ranging from 25° C. to 30° C.

*Root description*.—Medium to thick, slightly fleshy; typically pale creamy white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact to medium-sized, broadly upright and uniformly mounded plant habit; inverted triangle with rounded crown; large full inflorescences positioned above the foliar plane; moderately vigorous growth habit and moderate growth rate.

*Plant height, soil level to top of floral plane*.—About 25 cm.

*Plant diameter or spread*.—About 50 cm.

*Lateral branch description*.—Branching habit: Freely branching habit with about six to eight lateral branches developing after pinching. Length: About 23 cm. Diameter: About 6 mm. Internode length: About 8 mm to 15 mm. Strength: Strong. Texture and luster: Smooth, glabrous; glossy. Color: Close to 146A.

*Leaf description*.—Arrangement: Alternate, simple. Length: About 12 cm to 14 cm. Width: About 7 cm to 10 cm. Shape: Ovate. Apex: Acuminate. Base: Cuneate. Margin: One to two shallow lobes. Venation pattern: Pinnate. Texture and luster, upper surface: Smooth, glabrous; moderately glossy. Texture and luster, lower surface: Smooth, glabrous; matte. Color: Developing leaves, upper surface: Close to between 144A and 137B. Developing leaves, lower surface: Close to 137B to 137C. Fully expanded leaves, upper surface: Close to 139A; venation, close to 146A. Fully expanded leaves, lower surface: Close to 137A; venation, close to 146B. Petioles: Length: About 4.5 cm to 6 cm. Diameter: About 2.5 mm to 3 mm. Strength: Moderately strong. Texture and luster, upper and lower surfaces: Smooth, glabrous; glossy. Color, upper surface: Close to 146A. Color, lower surface: Close to 146B.

Inflorescence description:

*Inflorescence type and habit*.—Large full inflorescences are compound corymbs of cyathia with colored flower bracts subtending the cyathia; one inflorescence per lateral branch with inflorescences positioned above and beyond the foliar plane.

*Fragrance*.—None detected.

*Natural flowering season*.—Plants flower naturally during the late autumn to winter under long nyctoperiod conditions; inflorescence initiation and development can be induced under artificial long nyctoperiod conditions; response time is about 7.5 to 8 weeks.

*Post-production longevity*.—Excellent post-production longevity; plants of the new Poinsettia maintain good substance and bract color for about four to six weeks; flower bracts persistent.

*Inflorescence width*.—About 25 cm.

*Inflorescence height*.—About 2.5 cm to 3 cm.

*Flower bracts*.—Quantity per inflorescence: About 15. Length: About 11.5 cm to 12.5 cm. Width: About 7 cm to 9 cm. Shape: Ovate. Apex: Acuminate with an elongated apex. Base: Cuneate. Margin: Entire or occasionally lobed. Aspect: Horizontal to slightly upright. Venation: Pinnate. Texture and luster, upper and lower surfaces: Moderately rugose, glabrous; matte. Color: Developing bracts, upper and lower surfaces: Close to 8D. Fully expanded bracts, upper and lower surfaces: Close to 10D; venation, close to 10D; color becoming closer to 11C with development. Bract petioles: Length: About 2.2 cm. Diameter: About 2 mm. Texture and luster, upper and lower surfaces: Smooth, glabrous; glossy. Color, upper and lower surfaces: Close to 154C.

*Cyathia*.—Quantity per corymb: About five to eight. Length: About 5 mm. Width: About 4 mm. Shape: Cylindrical to ovate. Texture and luster, inner and outer surfaces: Smooth, glabrous; matte. Color, developing, inner and outer surfaces: Close to 144B. Color, fully developed, inner and outer surfaces: Close to 145A. Nectaries: Quantity per cyathium: Typically one. Length: About 3 mm. Diameter: About 2 mm. Shape: Lip-shaped. Texture and luster, inner and outer surfaces: Smooth, glabrous; matte. Color, fully developed, inner surface: Close to 14A. Color, fully developed, outer surface: Close to 13B.

*Pedicels*.—Length: About 1 mm to 2 mm. Diameter: About 1 mm. Strength: Moderately strong. Texture and luster: Smooth, glabrous; glossy. Color: Close to 145A.

*Reproductive organs*.—Stamens: To date, stamen development has not been observed on plants of the new Poinsettia. Pistils: Quantity per cyathia: About two to three. Pistil length: About 3 mm to 4 mm. Style length: About 2 mm to 3 mm. Style shape: Recurved. Fruits: Quantity: None to very few with none to three seeds. Length: About 8 mm to 12 mm. Diameter: About 6 mm to 10 mm. Texture: Smooth, glabrous.

Pathogen & pest resistance: Plants of the new Poinsettia have not been shown to be resistant to pathogens and pests common to Poinsettia plants.

It is claimed:

1. A new and distinct Poinsettia plant named 'LAZZPO1315' as illustrated and described.

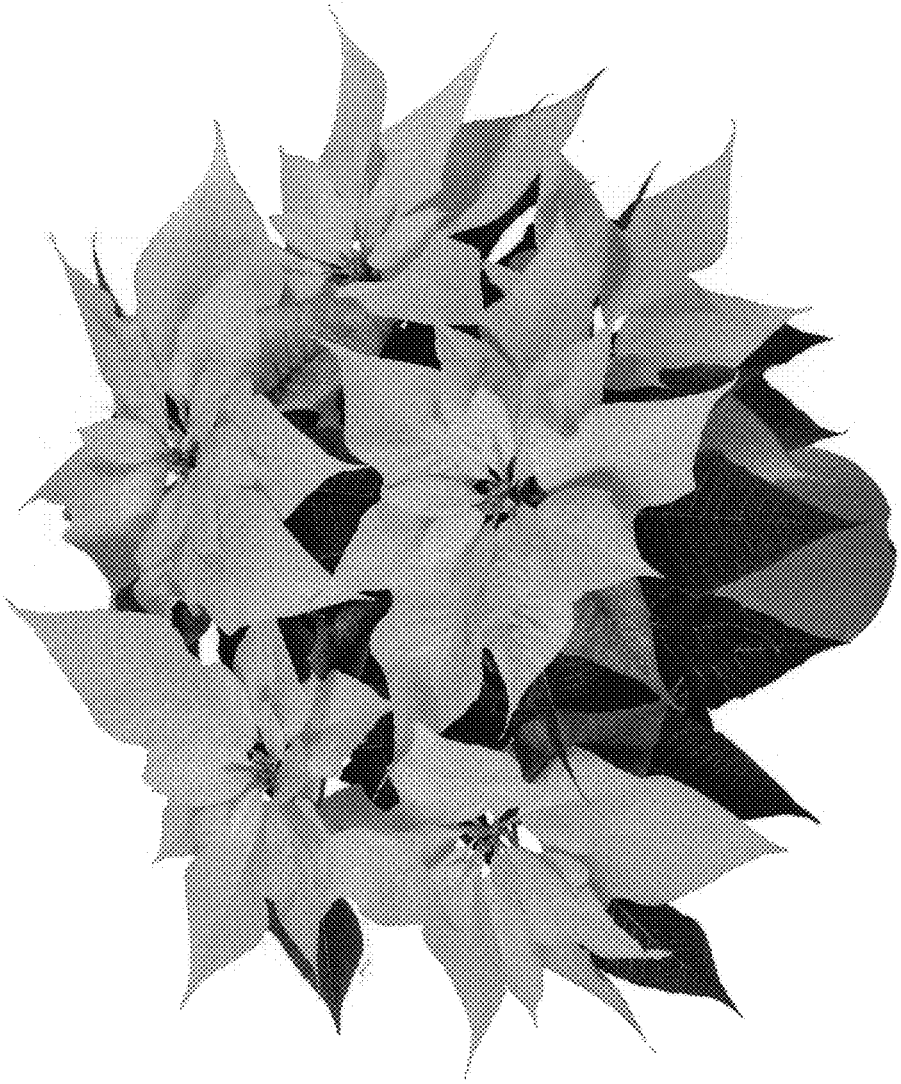

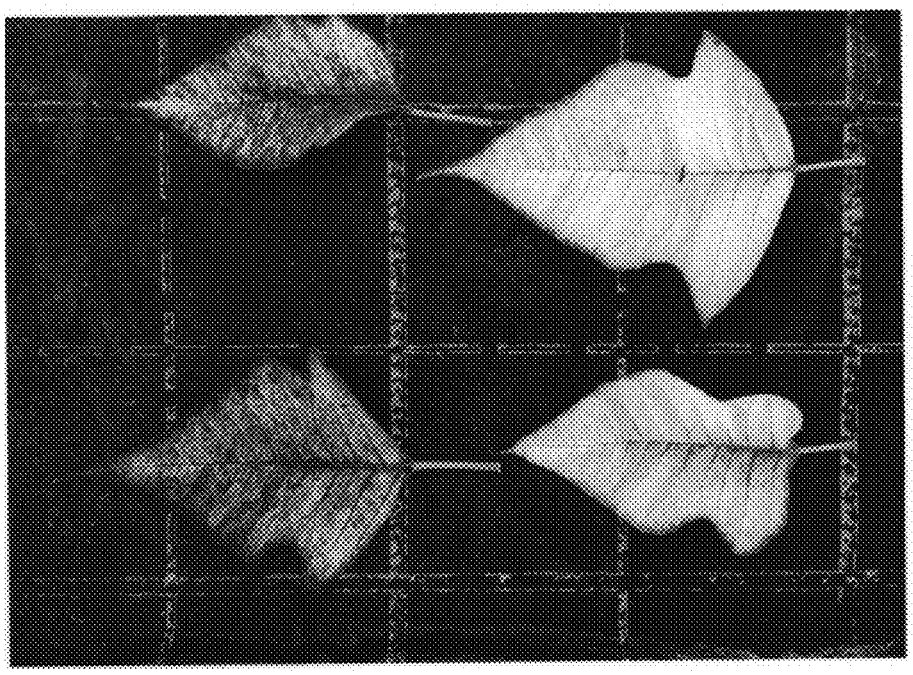
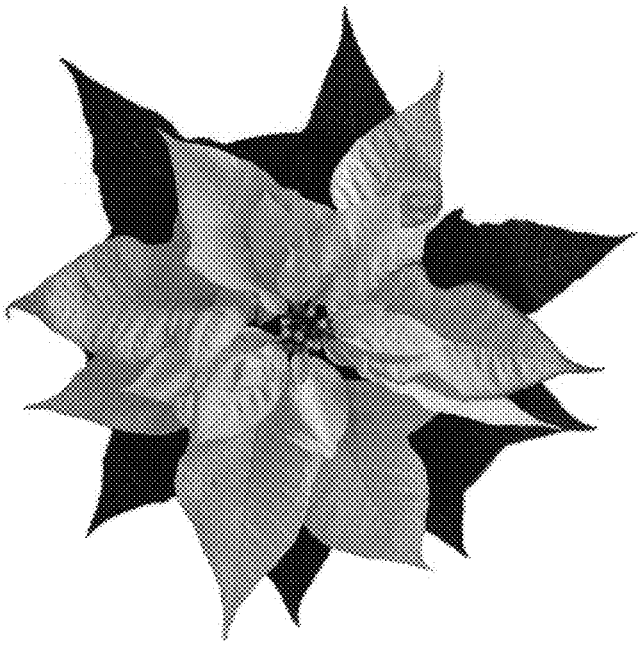

* * * * *